United States Patent [19]

Boswell et al.

[11] Patent Number: 4,668,676
[45] Date of Patent: May 26, 1987

[54] AZAPROPAZONE PREVENTION OF POST-ISCHEMIC TISSUE DAMAGE

[75] Inventors: George A. Boswell, Wilmington, Del.; William M. Mackin, Lincoln University, Pa.; Martin J. Thoolen, Newark, Del.

[73] Assignee: E.I. Du Pont de Nemours and Company, Wilmington, Del.

[21] Appl. No.: 885,766

[22] Filed: Jul. 15, 1986

Related U.S. Application Data

[63] Continuation-in-part of Ser. No. 805,710, Dec. 6, 1985, abandoned.

[51] Int. Cl.$^4$ .............................................. A61K 31/53
[52] U.S. Cl. .................................................... 514/243
[58] Field of Search ......................................... 514/243

[56] References Cited

U.S. PATENT DOCUMENTS 3,349,088 10/1967 Molnar et al. ...................... 260/248
3,482,024 12/1969 Molnar et al. ...................... 424/249
4,305,942 12/1981 Thiele et al. ........................ 424/249

OTHER PUBLICATIONS

McCord, J. M.: "Oxygen-Derived Free Radicals in Post-Ischemic Tissue Injury," New England Journal of Medicine, 312:154-163, 1985.
Hill, J. H., et al.: "The Phlogistic role of C3 Leukotactic Fragments in Myocardial Infacts of Rats," Journal Exp. Medicine, 133:885-900, 1971.
Rossen, R. D., et al.: "Selective Accumulation of First Component of Complement and Leukocytes in Ischemic Canine Heart Muscle," Cir. Res. 57:119-129, 1985.
Bednar, M., et al.: "Nafazatrom-Induced Salvage of Ischemic Myocardium in Anesthetized Dogs is Mediated Through Inhibition of Neutrophil Function," Circ. Res. 57:131-141, 1985.
Templeton, J. S.: "Azapropazone, in *Anti-Rheumatic Drugs,*" vol. 3 (Edited by E. C. Huskisson), Praeger Publishers, New York, p. 97 (1983).
Bulkley, G. B.: "Role of Oxygen-Derived Free Radicals in Human Diseases: Immediate and Long Range Applications for Antioxidant Therapy in Clinical Medicine," Program & Abstracts, 19th National Medicinal Chemistry Symposium, Tuscon, Arizona, Jun. 17-21, 1984.
Jones, H. P., et al., "Effect of Allopurinol of Neutrophil Superoxide Production, Chemotaxis or Degranulation," *Biochemical Pharmacology,* vol. 34, No. 20, pp. 3673-3676, 1976.

Primary Examiner—Stanley J. Friedman

[57] ABSTRACT

Azapropazone can be used to prevent post-ischemic tissue damage in mammals.

2 Claims, No Drawings

AZAPROPAZONE PREVENTION OF POST-ISCHEMIC TISSUE DAMAGE

CROSS REFERENCE TO RELATED APPLICATIONS

This application is a continuation-in-part of copending application Ser. No. 805,710, filed Dec. 6, 1985, now abandoned.

BACKGROUND OF THE INVENTION

1. Field of the Invention

This invention relates to the prevention of post-ischemic tissue damage.

2. Description of the Prior Art

Ischemic and post-ischemic tissue damage results when blood flow into bodily tissues and/or organs is blocked and the tissue becomes hypoxic. Upon restoration of normal blood flow, i.e., reperfusion, large amounts of toxic oxygen free radicals ($O_2^-$) are produced which cause significant tissue and/or organ damage and impaired function. Ischemia-induced tissue damage is now believed to be a major and medically significant complication in a wide variety of cardiovascular, central nervous system, and intestinal disease processes. In addition, post-ischemic tissue damage is also a medically significant problem in organ transplantation and circulatory shock. (McCord, J. M.: "Oxygen-Derived Free Radicals in Post-Ischemic Tissue Injury," New England Journal of Medicine, 312:154–163, 1985.)

The toxic oxygen radicals responsible for post-ischemic tissue injury originate from two biochemically different sources. Large amounts of radicals are produced in ischemic and reperfused tissue as a byproduct of the enzymatic conversion of hypoxanthine to xanthine by xanthine oxidase and also as metabolic products from activated blood neutrophils also known as activated polymorphonuclear leukocytes. There is substantial experimental evidence implicating both sources as major contributors to the pathology of ischemia-reperfusion tissue damage. (Hill, J. H., Ward, P.A.: "The Phlogistic Role of C3 Leukotactic Fragments in Myocardial Infarcts of Rats," Journal Exp. Medicine, 133:885–900, 1971; Rossen, R. D. et al: "Selective Accumulation of First Component of Complement and Leukocytes in Ischemic Canine Heart Muscle," Circ. Res. 57:119–129, 1985; Bednar, M., Smith, B., Pinto, A. and Mullane, K. M.: "Nafazatrom-Induced Salvage of Ischemic Myocardium in Anesthetized Dogs is Mediated Through Inhibition of Neutrophil Function," Circ. Res. 57:131–141, 1985.) Moreover, in myocardial ischemia due to permanent occlusion of a coronary artery, oxygen free radicals and neutrophils are believed to cause tissue damage. The oxygen free radicals would be generated in ischemic tissue from oxygen delivered to the tissue via the coronary collateral circulation (Downey et al: "Infarct size limitation by the xanthine oxidase inhibitor allopurinol in closed chest dogs with small infarcts", Cardiovasc. Res. 19, 686–698, 1985.).

Therapeutic approaches to treating post-ischemic tissue injury have concentrated initially on drugs that selectively inhibit xanthine oxidase (e.g., allopurinol) and, more recently, on drugs that inhibit $O_2^-$ production by activated polymorphonuclear leukocytes (e.g., aprotinin, nafazatrom, ibuprofen). Presently, there are no reports in the literature of any drug that inhibits post-ischemic tissue damage by inhibiting both xanthine oxidase and $O_2^-$ production by activated polymorphonuclear leukocytes.

Azapropazone is a nonsteroidal anti-inflammatory drug efficacious in treating gouty arthritis by virtue of its ability to inhibit xanthine oxidase and increase the renal excretion of uric acid (Templeton, J. S.: "Azapropazone, In *Anti-Rheumatic Drugs,*" Vol. 3 (Edited by E. C. Huskisson), Praeger Publishers, New York, p. 97 (1983); U.S. Pat. Nos. 3,349,088, 3,482,024, and 4,305,942).

It has now been found that azapropazone also has the unique feature of inhibiting a variety of neutrophil functional responses including the generation of oxygen free radicals. Moreover, the concentrations of azapropazone found to inhibit neutrophil $O_2^-$ production as well as xanthine oxidase in vitro correlate well with the therapeutic plasma levels attained in man. Based upon azapropazone's ability to inhibit both sources of toxic $O_2^-$ radicals, this drug will have distinct and novel therapeutic advantage over the current therapies used in treating ischemic and post-ischemic tissue damage. Specifically, azapropazone would be beneficial in myocardial ischemia and reperfusion due to occlusion and subsequent recanalization of one or more coronary arteries, as well as in myocardial damage due to coronary artery occlusion by itself.

SUMMARY OF THE INVENTION

The damage occurring in ischemic and upon reperfusion of ischemic mammalian tissue can be prevented by administering to the mammal the compound 3-dimethylamino-7-methyl-1,2-(n-propylmalonyl)-1,2-dihydro1,2,4-benzotriazine dihydrate. This compound has the formula:

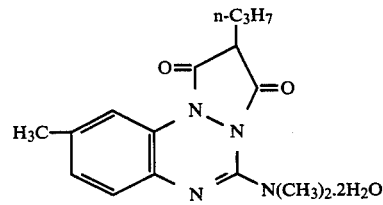

The compound is known by the WHO recommended International Nonproprietary Name (INN) "Azapropazone." Azapropazone is applied in an amount sufficient to reduce ischemic and reperfusion damage by inhibiting both xanthine oxidase and $O_2^-$ production by activated polymorphonuclear leukocytes. The exact amount will depend on the nature of the ischemia and the rate of reperfusion following ischemia.

DETAILED DESCRIPTION OF THE INVENTION

Azapropazone will have therapeutic utility in a wide variety of disease states in which ischemia-reperfusion tissue damage is medically significant. Specific disease processes in which azapropazone would be efficacious are intestinal, myocardial, cerebral ischemia as well as in circulatory shock, frostbite and organ transplantation. Based upon its pharmacokinetic profile, azapropazone will be administered orally or as intravenous injections with doses ranging between 300–1800 mg/day in man. Azapropazone therapy will be short or long term depending upon the disease being treated. Azapropazone may also be administered prophylactically to patients judged to be at high risk of ischemic attack.

Azapropazone can be manufactured as taught in U.S. Pat. No. 3,349,088 which is incorporated by reference. The active compound can be formulated as taught in U.S. Pat. No. 4,305,942, also incorporated by reference. Particularly preferred is an injectible formulation for ease of administration to unconscious patients or in emergency situations.

EXAMPLE 1

Azapropazone can be formulated for injection as follows:

| | |
|---|---|
| Azapropazone dihydrate (corresponding to 576.8 mg azapropazone sodium) | 600.0 mg |
| Manitol | 30.0 mg |
| Sodium metabisulfite | 3.0 mg |
| Sodium hydroxide to adjust pH | 72.0 mg |
| Water for injection | 5.0 ml |

EXAMPLE 2

Azapropazone can be formulated as a 300 mg capsule as follows:

| | |
|---|---|
| Azapropazone dihydrate | 300 mg |
| Sodium lauryl sulfate, NF | 4.2 mg |
| Povidone U.S.P. | 3.0 mg |
| Silicon dioxide, NF | 1.8 mg |
| Calcium stearate | 4.5 mg |

Form uniform aggregate with sufficient equal amounts of denatured alcohol and purified water, dry and mill the aggregates to the desired size. Insert the resulting powder into a hard opaque gelatin capsule containing approved colorants.

EXAMPLE 3

The following experiments were performed to demonstrate azapropazone inhibition of $O_2^-$ production by polymorphonuclear leukocytes. Rat peritoneal neutrophils (PMN) were collected 4–6 hrs. after i.p. injection of 10% w/v sodium caseinate (Sigma) and washed several times with Hanks' buffer (pH 7.2) at 4° C. to remove residual exudate fluids. The cells were stimulated to generate $O_2^-$ by exposing the cells to 100 ng/ml phorbol-12-myristate-13-acetate (PMA) in dimethylsulfoxide. PMN ($5 \times 10^6$ cells/ml) were pretreated with or without varying concentrations of azapropazone for 10 minutes at 37° C. Non-reduced cytochrome C (0.23 mM) and PMA (100 ng/ml) were added to the cells and the mixture quickly transferred to quartz curvettes in a Beckman Du-6 spectrophotometer at 37° C. Superoxide anion ($O_2^-$) generation was assayed by measuring the $O_2^-$ dependent reduction of ferricytochrome C to ferrocytochrome C by monitoring absorbance at 550 nm over a 30 min. period. In order to calculate specific $O_2^-$ reduced cytochrome C, the change in Abs at 550 nm detected in the presence of 30 μg/ml superoxide dismutase (SOD) was also measured. Data were converted to nanomoles of $O_2^-$ reduced cytochrome C by first subtracting the SOD values and then dividing by the absorbance coefficient for reduced cytochrome C (21.2 $mM^{-1} cm^{-1}$). Rates of $O_2^-$ production were calculated by linear regression analysis of the $O_2^-$ production vs. time curve at times between 0 and 15 minutes. All data are expressed as mean values of 3 or more separate experiments. It can be seen that azapropazone causes significant inhibition of both the rate of $O_2^-$ generation and maximal amounts of $O_2^-$ produced by PMN stimulated with PMA.

Inhibition of Rat PMN $O_2$ Production By Azapropazone

| Treatment | nmoles Cyto C reduced/$5.0 \times 10^6$ PMN (minute) | | | | | |
|---|---|---|---|---|---|---|
| | 0 | 5 | 10 | 15 | 20 | 30 |
| + PMA | 1.6± 1.3 | 5.4± 1.2 | 7.5± 1.6 | 7.8± 2.1 | 8.3± 2.4 | 8.1± 2.7 |
| − PMA | 0.3± 0.6 | 0.4± 0.4 | 0.5± 2.4 | 0.4± 0.8 | 0.1± 1.1 | 0.2± 1.8 |
| PMA + 0.1 mM azapropazone | 0.3± 0.6** | 2.6± 1.4* | 3.8± 1.6** | 4.5± 2.0** | 5.6± 2.4 | 4.8± 1.6 |
| PMA + 0.01 mM azapropazone | 0.3± 0.2** | 4.7± 2.7 | 7.0± 3.8 | 8.3± 4.4 | 9.1± 4.4 | 9.7± 5.9 |
| PMA + 0.001 mM azapropazone | 0.2± 0.5** | 4.9± 3.2 | 6.7± 4.4 | 8.7± 5.6 | 8.7± 5.6 | 8.7± 6.2 |

*Significantly different from untreated, PMA stimulated PMN by paired t-test at $p \leq 0.005$.
**Significantly different from untreated, PMA stimulated PMN by paired t-test at $p \leq 0.05$.

What is claimed is:

1. A method of preventing ischemic and post-ischemic tissue damage in a mammal comprising administering to the mammal suffering from or at risk of suffering from ischemia an amount of azapropazone sufficient to inhibit xanthine oxidase and $O_2^-$ production by activated polymorphonuclear leukocytes.

2. The method of claim 1 wherein the azapropazone is administered by injection.

* * * * *